(12) United States Patent
Dick

(10) Patent No.: US 7,043,298 B2
(45) Date of Patent: May 9, 2006

(54) ELECTROTHERAPY BY BONE CONDUCTION

(76) Inventor: Robert Van Dick, 10110 Loving Rd., Morganton, GA (US) 30560

(*) Notice: Subject to any disclaimer, the term of this patent is extended or adjusted under 35 U.S.C. 154(b) by 683 days.

(21) Appl. No.: 10/199,841

(22) Filed: Jul. 18, 2002

(65) Prior Publication Data

US 2004/0034395 A1   Feb. 19, 2004

(51) Int. Cl.
*A61N 1/32* (2006.01)
(52) U.S. Cl. ............... 607/2; 607/45; 607/46; 607/66; 607/148; 607/149
(58) Field of Classification Search ............ 607/45–46, 607/66–76, 148–149
See application file for complete search history.

(56) References Cited

U.S. PATENT DOCUMENTS

| 4,148,321 | A | * | 4/1979 | Wyss et al. ................... 607/67 |
| 4,535,775 | A | * | 8/1985 | Brighton et al. .............. 607/51 |
| 5,503,157 | A | * | 4/1996 | Sramek ....................... 600/506 |
| 5,512,057 | A | * | 4/1996 | Reiss et al. ................... 607/67 |
| 5,690,692 | A | * | 11/1997 | Fleming ...................... 607/50 |
| 6,304,782 | B1 | * | 10/2001 | Van Dick .................... 607/45 |
| 6,336,045 | B1 | * | 1/2002 | Brooks ....................... 600/547 |
| 6,473,643 | B1 | * | 10/2002 | Chai et al. .................. 600/547 |

\* cited by examiner

*Primary Examiner*—Robert Pezzuto
*Assistant Examiner*—Shevon Johnson
(74) *Attorney, Agent, or Firm*—Baker Donelson

(57) ABSTRACT

Pathological conditions are alleviated by bone conduction practiced by the application of sinusoidal electric waves at frequencies of between 4,200 and 6,500 hertz at less than 200 microamperes current.

2 Claims, No Drawings

ELECTROTHERAPY BY BONE CONDUCTION

TECHNICAL FIELD

This invention relates generally to therapeutic protocols and particularly to the electro-therapeutic treatment of physiological malconditions using bone conduction.

BACKGROUND OF THE INVENTION

Heretofore it has been recognized that acoustical waves can be generated and conducted through human skeletal structures for utilitarian purposes. This is generally referred to as bone conduction. The principal use to date of bone conduction has been the conduction of sound to the inner ear via the skull. This has found use in industries where workers are exposed to high noise background levels. This has also found use in military applications where communication needs to be inaudible to the naked ear.

SUMMARY OF THE INVENTION

It has now been discovered that certain medical conditions can be treated using principles of bone conduction. More specifically, it has been found that certain pathological conditions may be alleviated by the application of sinusoidal electric waves at frequencies that are dictated by and dependent upon the specific condition and its anatomical location. The frequency range is 4,200 to 6,500 hertz at less than 200 microamperes current. It has also been found that physiological stress induced by the malady may also be alleviated by this treatment. Although much remains in understanding the mechanics by which this procedure works, it is believed that resonance probably plays a role since different physical organ conditions, with their different cellular sizes and shapes, require different treatment frequencies. Advantageously, the method may be practiced in conjunction with electrotherapy by bloodstream conduction without relocation of the electrodes attached to the body.

DETAILED DESCRIPTION

The electrical therapy is applied to body bone preferably with electrodes secured to the skin over the right and left wrists, arms, ankles or legs for four minutes or less. The electrodes are coupled to a 10-volt peak-to-peak signal AC source that provides 200 microamperes or less current. A sinusoidal waveform is used at a frequency of between 4,200 Hz and 6,500 Hz, depending on the condition to be treated. Preferably, variations in signal amplitude are limited to plus or minus 10%. The source impedance of the signal generated is between 18,000 and 20,000 ohms, and is floating. By not being grounded stray 60 Hz signals are avoided from being mixed with the generated signal. Preferably, one treatment session is had per day although two may be had if spaced by at least seven hours. When accompanied with electrotherapy by blood conduction such is applied to the upper torso by electric contacts applied to the skin of finger, hands, wrists, arms or the armpits for a period of time sufficient to be applied to most of the patient's circulating blood.

The effective frequency for given conditions have been determined by trial and error. The frequencies listed in Table 1 have been determined empirically with frequency tolerance being +/−6 Hz and with the number of sessions identified being typical.

TABLE 1

| Bone conduction only: (4 minutes per treatment, 7 hours apart between treatments) | |
|---|---|
| Adult diabetes - | 5,620 Hz, 30 sessions. |
| Asbestos in lungs - | 5,111 Hz, 10 sessions. |
| Eye cataracts - | 6,110 Hz, 7 sessions. |
| Bone spurs - | 4,931 Hz, 4 sessions. |
| Clogged sinuses - | 5,009 Hz, 4 sessions. |
| Near-sighted & far-sighted eyes - | 6,075 Hz, 6 sessions. |
| Artery plaque - | 5,885 Hz, 11 sessions - then 4,632 Hz, 15 sessions - then 5,364 Hz, 21 sessions. |
| Blood conduction followed by bone conduction: (20 minutes typical for blood treatments, 4 minutes for bone treatments) | |
| Lung fungus - | (blood) 3,481 Hz, and immediately - (bone) 4,902 Hz, 8 sessions. |
| Brain fungus - | (blood) 2,608 Hz only, 10 sessions or more until completed. Then - (blood) - 3,545 Hz, and immediately - (bone) 5,085 Hz, 10 sessions. |
| Glaucoma - | (blood) 3,022 Hz, - and immediately (bone) 6,023 Hz, 7 sessions. |
| Sluggish colon - | (blood) 4,628 Hz, - and immediately (bone) 6,010 Hz, 8 sessions. |
| Cancers - | (blood) 3,022 Hz, then 7 hours later - (bone) 5,122 Hz, 17 sessions. |

The frequencies listed in Table 2 has not yet been determined empirically but are, based on the experience gained to date empirically above, believed to be effective.

TABLE 2

| Bone conduction only: (4 minutes per treatment, 7 hours apart between treatments) | |
|---|---|
| Children diabetes - | 5,023, 21 sessions. |
| Lumbar vertebrae, compression - | 6,110 Hz, 8 sessions. |
| Hip ligaments, unbalanced tensions - | 5,403 Hz, 6 sessions. |
| Hip ligaments, irritated - | 5,120 Hz, 9 sessions. |
| Sacrum nerves, irritated - | 6,103 Hz, 10 sessions. |
| Weak heart muscle - | 6,022 Hz, 11 sessions. |
| Calcium on heart valve - | 6,004 Hz, 10 sessions (much water needed after each session). |
| Clogged auditory tubes - | 5,092 Hz, 7 sessions. |
| Leaky gut - | 6,033 Hz, 14 sessions. |
| TMJ relaxation - | 6,005 Hz, 6 sessions. |
| Blood Conduction followed by bone conduction: (20 minutes typical for blood treatments, 4 minutes for bone treatments) | |
| Chronic fatigue syndrome - | (blood) 3,902 Hz, then 3 hours later - (bone) 6,123 Hz, 10 sessions. |
| Pre-menstrual syndrome - | (blood) 3,040 Hz, and immediately - (bone) 5,932 Hz, 10 sessions. |

Those conditions for which a single frequency application was found to be effective are believed to involve principally bone conduction. Those that require more than one frequency appear also to involve bloodstream conduction. The application time for bone conduction should be limited to four minutes to avoid interference with normal bone marrow blood cell production. Thus it is advisable not to treat physical conditions that affect bone marrow blood production such as leukemia, bone cancer and lymphatic system cancer.

When the electrotherapy by bone conduction may be practiced in conjunction with electrotherapy by bloodstream conduction, the latter is preferably practiced as described in U.S. Pat. No. 6,304,782. Sinusoidal alternating current is used in a range of between 2,000 Hz and 6,000 Hz. The source impedance of the signal is between 8,000 and 12,000 ohms, floating. It is believed that with the combination of therapy the blood conduction therapy should be practiced before the bone conduction therapy.

Actual chemical tests have included a male that was treated in Georgia for a lung fungus condition. Following treatment all symptoms were gone and breathing was markedly improved. Maintenance treatments are conducted periodically due to the presence of fungi in the patient's home environment.

Brain fungus in a male was treated in California. Upon completion the symptoms were gone, headaches ceased. The patient also sleeps better and has a clearer mind. Brain fungus in a female was treated in South Carolina with the same results.

Testicular cancer was treated in a patient that resulted in the abatement of all symptoms. Post treatment tests found no evidence of residual cancer.

An adult female was treated in Florida for adult diabetes. This resulted in a diminishing in the required doses of insulin and in a marked general improvement in health.

Following treatments of a male in Washington with asbestos in his lungs, breathing returned to normal.

A male was treated in Georgia for vertebrae bone spurs that succeeded in removal of the spurs.

It thus is seen that electrotherapy has now been discovered for numerous medical conditions by bone conduction. The treatment has not only been found to be effective for the physical condition but also for the physiological stress that accompanies such. Though the invention has been described in its preferred form, it should be understood that additions, modifications or deletions may be made without departure from the spirit and scope of the invention as set forth in the following claims.

The invention claimed is:

1. Electrotherapy by bone conduction wherein alternating sinusoidal current within a frequency range of 4,200 Hz to 6,500 Hz is applied to human skeletal structure at less than 200 microampers with two electrodes secured to two body limbs coupled to a 10-volt peak-to-peak signal AC source with source impedance of between 18,000 and 20,000 ohms.

2. Electrotherapy by bone conduction wherein alternating sinusoidal current within a frequency range of 4,200 Hz to 6,500 Hz is applied to human skeletal structure at less than 200 microampers through two electrodes after the application of electrotherapy by bloodstream conduction using sinusoidal alternating current within a frequency range of 2,000 Hz to 6,000 Hz wherein the electrodes are coupled to an AC source with source impedance of between 8,000 and 12,000 ohms for the bloodstream conduction electrotherapy and then with an AC source with source impedance of between 18,000 and 20,000 ohms for the bone conduction therapy.

* * * * *